(12) United States Patent
Robinson

(10) Patent No.: US 12,648,859 B2
(45) Date of Patent: Jun. 9, 2026

(54) IMPLANT FUSION DEVICE AND METHOD OF MANUFACTURING

(71) Applicant: Spectrum Spine IP Holdings, Inc., Inlet Beach, FL (US)

(72) Inventor: James C. Robinson, Inlet Beach, FL (US)

(73) Assignee: Spectrum Spine IP Holdings, Inc., Inlet Beach, FL (US)

( * ) Notice: Subject to any disclaimer, the term of this patent is extended or adjusted under 35 U.S.C. 154(b) by 0 days.

(21) Appl. No.: 18/339,577

(22) Filed: Jun. 22, 2023

(65) Prior Publication Data

US 2023/0414375 A1 Dec. 28, 2023

Related U.S. Application Data

(60) Provisional application No. 63/354,748, filed on Jun. 23, 2022.

(51) Int. Cl.
A61F 2/44 (2006.01)
B23K 26/362 (2014.01)
(Continued)

(52) U.S. Cl.
CPC .......... A61F 2/4455 (2013.01); B23K 26/362 (2013.01); B33Y 40/20 (2020.01);
(Continued)

(58) Field of Classification Search
CPC ............ A61F 2/4455; A61F 2002/3084; A61F 2002/3092; A61F 2002/3093;
(Continued)

(56) References Cited

U.S. PATENT DOCUMENTS

| | | | |
|---|---|---|---|
| 2,706,506 A | 4/1955 | Marcel | |
| 2,855,232 A | 10/1958 | Kozak | |

(Continued)

FOREIGN PATENT DOCUMENTS

| | | | |
|---|---|---|---|
| CN | 1678248 A | 10/2005 | |
| CN | 111728726 A | 10/2020 | |

(Continued)

OTHER PUBLICATIONS

Dumas et al.; Femtosecond laser nano/micro patterning of titanium influences mesenchymal stem cell adhesion and commitment; Biomedical Materials; 10(5); 055002; pp. 1-13; Sep. 3, 2015.

(Continued)

*Primary Examiner* — Christina A Johnson
*Assistant Examiner* — Kelsey C Grace
(74) *Attorney, Agent, or Firm* — Shay Glenn LLP

(57) ABSTRACT

The present invention relates to an implant fusion device and a method of manufacturing an implant fusion device. More particularly an orthopedic or spinal implant configured to be implanted between adjacent vertebrae or within a gap in a bone or between bones, the device having a manufactured body structure simulating the physical characteristics of trabecular bone, but with improved osteoinductive features on the exterior surface wherein the device is fabricated using 3D printing. Alternatively, the implant may be made through 3D printing in a manner that results in a relatively or completely solid structure, but with a surface that mimics trabecular bone structure.

26 Claims, 7 Drawing Sheets

(51) Int. Cl.

| | | |
|---|---|---|
| *B33Y 40/20* | (2020.01) |
| *B33Y 80/00* | (2015.01) |
| *A61F 2/30* | (2006.01) |
| *B33Y 10/00* | (2015.01) |

(52) U.S. Cl.

CPC ....... B33Y 80/00 (2014.12); *A61F 2002/3084* (2013.01); *A61F 2002/3092* (2013.01); *A61F 2002/3093* (2013.01); *A61F 2002/3097* (2013.01); *A61F 2002/30985* (2013.01); *B33Y 10/00* (2014.12)

(58) Field of Classification Search

CPC ... A61F 2002/3097; A61F 2002/30985; B33Y 80/00; B33Y 40/20; B33Y 10/00; B23K 26/362

See application file for complete search history.

(56) References Cited

U.S. PATENT DOCUMENTS

| | | | |
|---|---|---|---|
| 3,572,340 | A | 3/1971 | Lloyd et al. |
| 3,779,243 | A | 12/1973 | Oakes et al. |
| 3,901,298 | A | 8/1975 | Eby |
| 3,983,872 | A | 10/1976 | Nehring |
| 4,136,696 | A | 1/1979 | Nehring |
| 4,330,891 | A | 5/1982 | Branemark et al. |
| 4,392,858 | A | 7/1983 | George et al. |
| 4,435,171 | A | 3/1984 | Goldberg et al. |
| 4,457,755 | A | 7/1984 | Wilson |
| 4,545,374 | A | 10/1985 | Jacobson |
| 4,553,272 | A | 11/1985 | Mears |
| 4,569,674 | A | 2/1986 | Phillips et al. |
| 4,608,052 | A | 8/1986 | Van Kampen et al. |
| 4,640,271 | A | 2/1987 | Lower |
| 4,651,752 | A | 3/1987 | Fuerst |
| 4,653,489 | A | 3/1987 | Tronzo |
| 4,657,550 | A | 4/1987 | Daher |
| 4,723,913 | A | 2/1988 | Bergman |
| 4,759,769 | A | 7/1988 | Hedman et al. |
| 4,857,269 | A | 8/1989 | Wang et al. |
| 4,863,476 | A | 9/1989 | Sheppard |
| 4,929,247 | A | 5/1990 | Rayhack |
| 4,946,458 | A | 8/1990 | Hams et al. |
| 4,952,236 | A | 8/1990 | Wang et al. |
| 5,010,879 | A | 4/1991 | Moriya et al. |
| 5,141,503 | A | 8/1992 | Sewell, Jr. |
| 5,192,282 | A | 3/1993 | Draenert |
| 5,219,361 | A | 6/1993 | Von Recum et al. |
| 5,246,530 | A | 9/1993 | Bugle et al. |
| 5,281,222 | A | 1/1994 | Allard et al. |
| 5,282,861 | A | 2/1994 | Kaplan |
| 5,290,312 | A | 3/1994 | Kojimoto et al. |
| 5,312,405 | A | 5/1994 | Korotko et al. |
| 5,380,326 | A | 1/1995 | Lin |
| 5,473,138 | A | 12/1995 | Singh et al. |
| 5,490,962 | A | 2/1996 | Cima |
| 5,496,318 | A | 3/1996 | Howland et al. |
| 5,584,688 | A | 12/1996 | Sakuma |
| 5,603,338 | A | 2/1997 | Beaty |
| 5,628,733 | A | 5/1997 | Zinreich et al. |
| 5,630,817 | A | 5/1997 | Rokegem et al. |
| 5,645,540 | A | 7/1997 | Henniges et al. |
| 5,653,763 | A | 8/1997 | Errico et al. |
| 5,665,118 | A | 9/1997 | Lasalle et al. |
| 5,683,394 | A | 11/1997 | Rinner |
| 5,714,103 | A | 2/1998 | Bauer et al. |
| 5,716,412 | A | 2/1998 | DeCarlo et al. |
| D392,387 | S | 3/1998 | Michelson |
| 5,725,581 | A | 3/1998 | Brånemark |
| 5,800,550 | A | 9/1998 | Sertich |
| 5,860,977 | A | 1/1999 | Zucherman et al. |
| 5,928,139 | A | 7/1999 | Koros et al. |
| 5,965,006 | A | 10/1999 | Baege et al. |
| 6,039,761 | A | 3/2000 | Li et al. |
| 6,048,342 | A | 4/2000 | Zucherman et al. |
| 6,048,343 | A | 4/2000 | Mathis et al. |
| 6,068,630 | A | 5/2000 | Zucherman et al. |
| 6,102,950 | A | 8/2000 | Vaccaro |
| 6,129,872 | A | 10/2000 | Jang |
| 6,176,881 | B1 | 1/2001 | Schar et al. |
| 6,176,882 | B1 | 1/2001 | Biedermann et al. |
| 6,190,414 | B1 | 2/2001 | Young et al. |
| 6,193,757 | B1 | 2/2001 | Foley et al. |
| 6,210,413 | B1 | 4/2001 | Justis et al. |
| 6,214,012 | B1 | 4/2001 | Karpman et al. |
| 6,254,602 | B1 | 7/2001 | Justis |
| 6,261,276 | B1 | 7/2001 | Reitsma |
| 6,312,431 | B1 | 11/2001 | Asfora |
| RE37,665 | E | 4/2002 | Ralph et al. |
| 6,368,351 | B1 | 4/2002 | Glenn et al. |
| 6,375,683 | B1 | 4/2002 | Crozet et al. |
| 6,413,257 | B1 | 7/2002 | Lin et al. |
| 6,419,491 | B1 | 7/2002 | Ricci et al. |
| 6,419,705 | B1 | 7/2002 | Erickson |
| 6,436,140 | B1 | 8/2002 | Liu et al. |
| 6,454,807 | B1 | 9/2002 | Jackson |
| 6,491,695 | B1 | 12/2002 | Roggenbuck |
| 6,527,803 | B1 | 3/2003 | Crozet et al. |
| 6,562,074 | B2 | 5/2003 | Gerbec et al. |
| 6,582,431 | B1 | 6/2003 | Ray |
| 6,596,008 | B1 | 7/2003 | Kambin |
| 6,602,255 | B1 | 8/2003 | Campbell et al. |
| 6,641,614 | B1 | 11/2003 | Wagner et al. |
| 6,648,895 | B2 | 11/2003 | Burkus et al. |
| 6,648,917 | B2 | 11/2003 | Gerbec et al. |
| 6,652,495 | B1 | 11/2003 | Walker |
| 6,652,533 | B2 | 11/2003 | O'Neil |
| 6,652,584 | B2 | 11/2003 | Michelson |
| 6,679,890 | B2 | 1/2004 | Margulies et al. |
| 6,695,842 | B2 | 2/2004 | Zucherman et al. |
| 6,695,846 | B2 | 2/2004 | Richelsoph et al. |
| 6,716,247 | B2 | 4/2004 | Michelson |
| 6,755,835 | B2 | 6/2004 | Schultheiss et al. |
| 6,773,460 | B2 | 8/2004 | Jackson |
| 6,808,537 | B2 | 10/2004 | Michelson |
| 6,849,093 | B2 | 2/2005 | Michelson |
| 6,893,464 | B2 | 5/2005 | Kiester |
| 6,896,677 | B1 | 5/2005 | Lin |
| 6,902,547 | B2 | 6/2005 | Aves et al. |
| 6,911,030 | B1 | 6/2005 | Vanacker et al. |
| 6,951,627 | B2 | 10/2005 | Li et al. |
| 6,979,346 | B1 | 12/2005 | Hossainy et al. |
| 7,018,418 | B2 | 3/2006 | Amrich et al. |
| 7,029,473 | B2 | 4/2006 | Zucherman et al. |
| 7,048,736 | B2 | 5/2006 | Robinson et al. |
| D530,423 | S | 10/2006 | Miles et al. |
| 7,128,760 | B2 | 10/2006 | Michelson |
| 7,172,594 | B2 | 2/2007 | Biscup |
| 7,217,291 | B2 | 5/2007 | Zucherman et al. |
| 7,250,550 | B2 | 7/2007 | Overby et al. |
| 7,255,713 | B2 | 8/2007 | Malek |
| 7,264,620 | B2 | 9/2007 | Taylo |
| 7,306,628 | B2 | 12/2007 | Zucherman et al. |
| D566,276 | S | 4/2008 | Blain |
| 7,431,735 | B2 | 10/2008 | Liu et al. |
| 7,481,839 | B2 | 1/2009 | Zucherman et al. |
| 7,544,208 | B1 | 6/2009 | Mueller et al. |
| 7,608,062 | B2 | 10/2009 | Sweeney |
| 7,608,097 | B2 | 10/2009 | Kyle |
| 7,608,098 | B1 | 10/2009 | Stone et al. |
| 7,615,079 | B2 | 11/2009 | Flickinger et al. |
| 7,655,027 | B2 | 2/2010 | Michelson |
| 7,655,046 | B2 | 2/2010 | Dryer et al. |
| 7,674,297 | B2 | 3/2010 | Falahee |
| 7,682,937 | B2 | 3/2010 | Evertsen et al. |
| 7,722,674 | B1 | 5/2010 | Grotz |
| 7,727,233 | B2 | 6/2010 | Blackwell et al. |
| 7,758,648 | B2 | 7/2010 | Castleman et al. |
| 7,776,067 | B2 | 8/2010 | Jackson |
| 7,846,186 | B2 | 12/2010 | Taylor |
| 7,850,718 | B2 | 12/2010 | Beete et al. |
| 7,850,862 | B2 | 12/2010 | Amrich et al. |
| 7,857,815 | B2 | 12/2010 | Zucherman et al. |

(56) References Cited

U.S. PATENT DOCUMENTS

| | | | |
|---|---|---|---|
| 7,857,839 B2 | 12/2010 | Duong et al. |
| 7,866,313 B2 | 1/2011 | Isenberg et al. |
| 7,875,065 B2 | 1/2011 | Jackson |
| 7,879,096 B2 | 2/2011 | Dickson et al. |
| 7,887,588 B2 | 2/2011 | Rapp |
| 7,892,259 B2 | 2/2011 | Biedermann et al. |
| 7,892,286 B2 | 2/2011 | Michelson |
| 7,901,436 B2 | 3/2011 | Baccelli et al. |
| 7,951,412 B2 | 5/2011 | Justin et al. |
| 7,955,512 B2 | 6/2011 | Park et al. |
| 8,007,537 B2 | 8/2011 | Zucherman et al. |
| 8,034,110 B2 | 10/2011 | Garner et al. |
| 8,048,120 B1 | 11/2011 | Fallin et al. |
| 8,062,375 B2 | 11/2011 | Glerum et al. |
| 8,092,533 B2 | 1/2012 | Melkent |
| 8,092,534 B2 | 1/2012 | Eckhardt |
| 8,100,948 B2 | 1/2012 | Ensign et al. |
| 8,105,366 B2 | 1/2012 | Null et al. |
| 8,105,382 B2 | 1/2012 | Olmos et al. |
| 8,110,004 B2 | 2/2012 | Valdevit et al. |
| 8,123,782 B2 | 2/2012 | Altarac et al. |
| 8,187,255 B2 | 5/2012 | Weber et al. |
| 8,216,316 B2 | 7/2012 | Kirschman |
| 8,221,472 B2 | 7/2012 | Peterson et al. |
| 8,221,502 B2 | 7/2012 | Branch, Jr. |
| 8,246,682 B2 | 8/2012 | Slivka et al. |
| 8,257,398 B2 | 9/2012 | Jackson |
| 8,262,697 B2 | 9/2012 | Kirschman |
| 8,267,969 B2 | 9/2012 | Altarec et al. |
| 8,292,927 B2 | 10/2012 | Rouleau et al. |
| 8,292,958 B1 | 10/2012 | Bruffey et al. |
| 8,323,349 B2 | 12/2012 | Schmid |
| 8,343,224 B2 | 1/2013 | Lynn et al. |
| 8,366,777 B2 | 2/2013 | Matthis et al. |
| 8,382,801 B2 | 2/2013 | Lamborne et al. |
| 8,398,713 B2 | 3/2013 | Weiman |
| 8,414,654 B1 | 4/2013 | Ganey |
| 8,491,640 B1 | 7/2013 | Robinson |
| 8,496,706 B2 | 7/2013 | Ragab et al. |
| 8,603,142 B2 | 12/2013 | Robinson |
| 8,603,143 B2 | 12/2013 | Robinson |
| 8,673,011 B2 | 3/2014 | Theofilos et al. |
| 8,728,045 B2 | 5/2014 | Hu et al. |
| 8,764,444 B2 | 7/2014 | Hansson |
| 8,845,728 B1 | 9/2014 | Abdou |
| 8,852,279 B2 | 10/2014 | Weiman |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,065 B2 | 12/2014 | Robinson |
| 8,915,947 B2 | 12/2014 | Robinson |
| 8,926,704 B2 | 1/2015 | Glerum et al. |
| 8,940,049 B1 | 1/2015 | Jimenez et al. |
| 8,998,964 B2 | 4/2015 | Robinson |
| 9,078,767 B1 | 7/2015 | McLean |
| 9,107,708 B2 | 8/2015 | Robinson |
| 9,125,757 B2 | 9/2015 | Weiman |
| 9,278,011 B2 | 3/2016 | Robinson |
| 9,364,262 B2 | 6/2016 | Robinson |
| 9,445,919 B2 | 9/2016 | Palmatier et al. |
| 9,452,484 B2 | 9/2016 | Oliver Vargas |
| 9,486,328 B2 | 11/2016 | Jimenez et al. |
| 9,492,288 B2 | 11/2016 | Wagner et al. |
| 9,510,863 B2 | 12/2016 | Robinson |
| 9,522,070 B2 | 12/2016 | Flower et al. |
| 9,532,883 B2 | 1/2017 | Mcluen et al. |
| 9,549,824 B2 | 1/2017 | McAfee |
| 9,585,699 B2 | 3/2017 | Robinson |
| 9,585,766 B2 | 3/2017 | Robinson |
| 9,585,767 B2 | 3/2017 | Robinson |
| 9,668,876 B2 | 6/2017 | Blain et al. |
| 9,687,285 B2 | 6/2017 | Robinson |
| 9,717,540 B2 | 8/2017 | Robinson |
| 9,724,208 B2 | 8/2017 | Robinson et al. |
| 9,839,527 B2 | 12/2017 | Robinson |
| 9,839,528 B2 | 12/2017 | Weiman et al. |
| 9,925,295 B2 | 3/2018 | McEntire et al. |
| 9,937,053 B2 | 4/2018 | Melknet et al. |
| 9,968,380 B2 | 5/2018 | Robinson |
| 9,987,050 B2 | 6/2018 | Robinson |
| 9,987,143 B2 | 6/2018 | Robinson et al. |
| 10,098,757 B2 | 10/2018 | Logan et al. |
| 10,111,758 B2 | 10/2018 | Robinson |
| 10,111,760 B2 | 10/2018 | Knapp et al. |
| 10,154,911 B2 | 12/2018 | Predick et al. |
| 10,154,914 B2 | 12/2018 | Robinson |
| 10,159,583 B2 | 12/2018 | Dietzel et al. |
| 10,219,914 B2 | 3/2019 | Faulhaber |
| 10,285,824 B2 | 5/2019 | Robinson |
| 10,358,723 B2 | 7/2019 | Vaidyanathan et al. |
| 10,369,010 B2 | 8/2019 | Robinson et al. |
| 10,398,559 B2 | 9/2019 | Jones et al. |
| 10,398,567 B2 | 9/2019 | Robinson |
| 10,405,894 B2 | 9/2019 | Robinson |
| 10,478,311 B2 | 11/2019 | Miccio et al. |
| 10,500,059 B2 | 12/2019 | Grotz |
| 10,500,064 B2 | 12/2019 | Robinson |
| 10,561,456 B2 | 2/2020 | Cawley et al. |
| 10,575,964 B2 | 3/2020 | Robinson |
| 10,575,965 B2 | 3/2020 | Kim et al. |
| 10,603,093 B2 | 3/2020 | Lin et al. |
| 10,709,575 B2 | 7/2020 | Robinson |
| 10,751,943 B2 | 8/2020 | Grbic et al. |
| 10,786,874 B2 | 9/2020 | Guo et al. |
| 10,888,431 B1 | 1/2021 | Robinson |
| 11,051,951 B2 | 7/2021 | Robinson et al. |
| 11,083,595 B2 | 8/2021 | Robinson |
| 11,090,184 B1 | 8/2021 | Prody |
| 11,141,512 B2 | 10/2021 | Robinson |
| 11,166,824 B2 | 11/2021 | Miccio et al. |
| 11,419,735 B2 | 8/2022 | Barriero et al. |
| 11,523,915 B2 | 12/2022 | Robinson |
| 11,590,000 B2 | 2/2023 | Robinson |
| 11,607,476 B2 | 3/2023 | Snell et al. |
| 11,617,657 B2 | 4/2023 | Robinson |
| 11,771,528 B1 | 10/2023 | Robinson et al. |
| 12,016,990 B2 | 6/2024 | Robinson |
| 12,029,653 B1 | 7/2024 | McLean et al. |
| 12,161,565 B2 | 12/2024 | McLean et al. |
| 2001/0021852 A1 | 9/2001 | Chappius |
| 2001/0039454 A1 | 11/2001 | Ricci et al. |
| 2002/0052656 A1 | 5/2002 | Michelson |
| 2002/0055745 A1 | 5/2002 | Mckinley et al. |
| 2002/0077702 A1 | 6/2002 | Castro |
| 2002/0128713 A1 | 9/2002 | Ferree |
| 2002/0138146 A1 | 9/2002 | Jackson |
| 2002/0177897 A1 | 11/2002 | Michelson |
| 2003/0125741 A1 | 7/2003 | Biedermann et al. |
| 2003/0149438 A1 | 8/2003 | Nichols |
| 2003/0176925 A1 | 9/2003 | Paponneau |
| 2003/0191535 A1 | 10/2003 | Castro |
| 2004/0000540 A1 | 1/2004 | Soboyejo et al. |
| 2004/0087947 A1 | 5/2004 | Lim et al. |
| 2004/0097933 A1 | 5/2004 | Lourdel et al. |
| 2004/0153154 A1 | 8/2004 | Dinkelacker |
| 2004/0162618 A1 | 8/2004 | Mujwid et al. |
| 2004/0172134 A1 | 9/2004 | Berry |
| 2004/0225292 A1 | 11/2004 | Sasso et al. |
| 2005/0015149 A1 | 1/2005 | Michelson |
| 2005/0027292 A1 | 2/2005 | Bernard et al. |
| 2005/0096507 A1 | 5/2005 | Prosek |
| 2005/0143738 A1 | 6/2005 | Zucherman et al. |
| 2005/0203624 A1 | 9/2005 | Serhan et al. |
| 2005/0216002 A1 | 9/2005 | Simonson |
| 2005/0228385 A1 | 10/2005 | Lott et al. |
| 2005/0234555 A1 | 10/2005 | Sutton et al. |
| 2006/0000814 A1 | 1/2006 | Gu et al. |
| 2006/0085068 A1 | 4/2006 | Barry |
| 2006/0085070 A1 | 4/2006 | Kim |
| 2006/0122701 A1 | 6/2006 | Kiester |
| 2006/0129244 A1 | 6/2006 | Ensign |
| 2006/0149245 A1 | 7/2006 | Sweeney |
| 2006/0155285 A1 | 7/2006 | Anderson |

(56) References Cited

U.S. PATENT DOCUMENTS

| | | |
|---|---|---|
| 2006/0195017 A1 | 8/2006 | Shluzas et al. |
| 2006/0200186 A1 | 9/2006 | Marchek et al. |
| 2006/0200244 A1 | 9/2006 | Assaker |
| 2006/0229615 A1 | 10/2006 | Abdou |
| 2006/0241621 A1 | 10/2006 | Moskowitz et al. |
| 2006/0247632 A1 | 11/2006 | Winslow et al. |
| 2006/0253201 A1 | 11/2006 | McLuen |
| 2006/0264706 A1 | 11/2006 | Piskun |
| 2006/0264938 A1 | 11/2006 | Zucherman et al. |
| 2006/0276899 A1 | 12/2006 | Zipnick et al. |
| 2006/0293662 A1 | 12/2006 | Boyer et al. |
| 2006/0293756 A1 | 12/2006 | Felt |
| 2006/0293758 A1 | 12/2006 | Yang et al. |
| 2007/0010813 A1 | 1/2007 | Zucherman et al. |
| 2007/0027433 A1 | 2/2007 | Garcia et al. |
| 2007/0050036 A1 | 3/2007 | Felt et al. |
| 2007/0093817 A1 | 4/2007 | Barrus et al. |
| 2007/0093830 A1 | 4/2007 | Zucherman et al. |
| 2007/0118120 A1 | 5/2007 | Stevenson et al. |
| 2007/0208229 A1 | 9/2007 | Prusmack |
| 2007/0219634 A1 | 9/2007 | Greenhalgh et al. |
| 2007/0225785 A1 | 9/2007 | Park et al. |
| 2007/0233082 A1 | 10/2007 | Chin et al. |
| 2007/0255409 A1 | 11/2007 | Dickson et al. |
| 2007/0270827 A1 | 11/2007 | Lim et al. |
| 2007/0270968 A1 | 11/2007 | Baynham et al. |
| 2007/0276381 A1 | 11/2007 | Butler et al. |
| 2007/0276402 A1 | 11/2007 | Frankel et al. |
| 2008/0033438 A1 | 2/2008 | Frizzell |
| 2008/0140129 A1 | 6/2008 | Dalton |
| 2008/0147128 A1 | 6/2008 | Fritzinger et al. |
| 2008/0154314 A1 | 6/2008 | McDevitt |
| 2008/0161814 A1 | 7/2008 | McAllister et al. |
| 2008/0177271 A1 | 7/2008 | Yeh |
| 2008/0183211 A1 | 7/2008 | Lamborne et al. |
| 2008/0214898 A1 | 9/2008 | Warren |
| 2008/0216926 A1 | 9/2008 | Guo et al. |
| 2008/0234687 A1 | 9/2008 | Schaller et al. |
| 2008/0243185 A1 | 10/2008 | Felix et al. |
| 2008/0262511 A1 | 10/2008 | Delaney |
| 2008/0262555 A1 | 10/2008 | Assell et al. |
| 2008/0288071 A1 | 11/2008 | Biyani et al. |
| 2008/0306545 A1 | 12/2008 | Winslow et al. |
| 2009/0082810 A1 | 3/2009 | Bhatnagar et al. |
| 2009/0118765 A1 | 5/2009 | Mueller et al. |
| 2009/0138089 A1 | 5/2009 | Doubler et al. |
| 2009/0164017 A1 | 6/2009 | Sommerich et al. |
| 2009/0171389 A1 | 7/2009 | Sankaran |
| 2009/0198338 A1 | 8/2009 | Phan |
| 2009/0222100 A1 | 9/2009 | Cipoletti et al. |
| 2009/0248088 A1 | 10/2009 | Biedermann |
| 2009/0254123 A1 | 10/2009 | Pafford et al. |
| 2009/0264895 A1 | 10/2009 | Gasperut |
| 2009/0264927 A1 | 10/2009 | Ginsberg et al. |
| 2009/0281628 A1 | 11/2009 | Oglaza et al. |
| 2009/0287218 A1 | 11/2009 | Beger et al. |
| 2010/0003640 A1 | 1/2010 | Damstra et al. |
| 2010/0030065 A1 | 2/2010 | Farr et al. |
| 2010/0036419 A1 | 2/2010 | Patel et al. |
| 2010/0057127 A1 | 3/2010 | McGuire et al. |
| 2010/0057130 A1 | 3/2010 | Yue |
| 2010/0063590 A1 | 3/2010 | Cannestra |
| 2010/0087869 A1 | 4/2010 | Abdou |
| 2010/0087923 A1 | 4/2010 | Abdou |
| 2010/0198173 A1 | 8/2010 | Hu et al. |
| 2010/0204795 A1 | 8/2010 | Greenhalgh |
| 2010/0211113 A1 | 8/2010 | Olson et al. |
| 2010/0222816 A1 | 9/2010 | Gabelberger et al. |
| 2010/0234890 A1 | 9/2010 | Alamin et al. |
| 2010/0249933 A1 | 9/2010 | Trieu |
| 2010/0249934 A1 | 9/2010 | Melkent |
| 2010/0280614 A1 | 11/2010 | Castro |
| 2010/0286695 A1 | 11/2010 | Hannani et al. |
| 2010/0292796 A1 | 11/2010 | Greenhalgh et al. |
| 2011/0004256 A1 | 1/2011 | Biedermann et al. |
| 2011/0015746 A1 | 1/2011 | Melkent et al. |
| 2011/0022090 A1 | 1/2011 | Gordon et al. |
| 2011/0029020 A1 | 2/2011 | Gordon et al. |
| 2011/0034777 A1 | 2/2011 | Ames et al. |
| 2011/0034781 A1 | 2/2011 | Loftus et al. |
| 2011/0040336 A1 | 2/2011 | Hammill et al. |
| 2011/0060300 A1 | 3/2011 | Weig et al. |
| 2011/0060373 A1 | 3/2011 | Russell et al. |
| 2011/0066186 A1 | 3/2011 | Boyer et al. |
| 2011/0077687 A1 | 3/2011 | Thompson et al. |
| 2011/0087328 A1 | 4/2011 | Dickson et al. |
| 2011/0093074 A1 | 4/2011 | Glerum et al. |
| 2011/0098820 A1 | 4/2011 | Blackwell et al. |
| 2011/0137348 A1 | 6/2011 | Jackson |
| 2011/0144692 A1 | 6/2011 | Saladin et al. |
| 2011/0144766 A1 | 6/2011 | Kale et al. |
| 2011/0160772 A1 | 6/2011 | Arcenio et al. |
| 2011/0172774 A1 | 7/2011 | Varela |
| 2011/0172779 A1 | 7/2011 | Dickson et al. |
| 2011/0230965 A1 | 9/2011 | Schell et al. |
| 2011/0282453 A1 | 11/2011 | Greenhalgh et al. |
| 2011/0282459 A1 | 11/2011 | Mcclellan et al. |
| 2011/0307065 A1 | 12/2011 | Hsu et al. |
| 2011/0319936 A1 | 12/2011 | Gordon et al. |
| 2011/0319997 A1 | 12/2011 | Glerum et al. |
| 2012/0010471 A1 | 1/2012 | Mire et al. |
| 2012/0016418 A1 | 1/2012 | Chin et al. |
| 2012/0029569 A1 | 2/2012 | Lott et al. |
| 2012/0029637 A1 | 2/2012 | Ragab et al. |
| 2012/0059470 A1 | 3/2012 | Weiman |
| 2012/0071978 A1 | 3/2012 | Suedkamp et al. |
| 2012/0095561 A1 | 4/2012 | Voisard et al. |
| 2012/0101528 A1 | 4/2012 | Souza et al. |
| 2012/0109203 A1 | 5/2012 | Dryer et al. |
| 2012/0109307 A1 | 5/2012 | Drochner et al. |
| 2012/0121774 A1 | 5/2012 | Marjeram et al. |
| 2012/0123465 A1 | 5/2012 | Nihalani |
| 2012/0143341 A1 | 6/2012 | Zipnick |
| 2012/0150228 A1 | 6/2012 | Zappacosta et al. |
| 2012/0158059 A1 | 6/2012 | Freid et al. |
| 2012/0158061 A1 | 6/2012 | Koch et al. |
| 2012/0172932 A1 | 7/2012 | Biedermann et al. |
| 2012/0226314 A1 | 9/2012 | Chin et al. |
| 2012/0226356 A1 | 9/2012 | Hirschl |
| 2012/0232552 A1 | 9/2012 | Morgenstern Lopez et al. |
| 2012/0245695 A1 | 9/2012 | Simpson et al. |
| 2012/0253406 A1 | 10/2012 | Bae et al. |
| 2012/0265204 A1 | 10/2012 | Schmierer et al. |
| 2012/0265257 A1 | 10/2012 | Jackson |
| 2012/0265309 A1 | 10/2012 | Glerum et al. |
| 2012/0310349 A1 | 12/2012 | Gordon et al. |
| 2012/0312778 A1* | 12/2012 | Ullrich, Jr. ............. C23C 14/34 |
| | | 451/28 |
| 2012/0316650 A1 | 12/2012 | Ullrich et al. |
| 2013/0023994 A1 | 1/2013 | Glerum |
| 2013/0023997 A1 | 1/2013 | Razain et al. |
| 2013/0072984 A1 | 3/2013 | Robinson |
| 2013/0085572 A1 | 4/2013 | Glerum |
| 2013/0103153 A1 | 4/2013 | Blackwell et al. |
| 2013/0110243 A1 | 5/2013 | Patterson et al. |
| 2013/0123925 A1 | 5/2013 | Patterson et al. |
| 2013/0138214 A1 | 5/2013 | Greenhalgh et al. |
| 2013/0144388 A1 | 6/2013 | Emery et al. |
| 2013/0158663 A1 | 6/2013 | Miller et al. |
| 2013/0158667 A1 | 6/2013 | Tabor et al. |
| 2013/0197642 A1 | 8/2013 | Ernst |
| 2013/0211525 A1 | 8/2013 | Mcluen et al. |
| 2013/0211526 A1 | 8/2013 | Alheidt et al. |
| 2013/0245770 A1 | 9/2013 | Felt et al. |
| 2013/0310948 A1 | 11/2013 | Luscher |
| 2014/0005727 A1 | 1/2014 | Kraemer |
| 2014/0012380 A1 | 1/2014 | Laurence et al. |
| 2014/0039622 A1 | 2/2014 | Glerum et al. |
| 2014/0046447 A1 | 2/2014 | Dunworth et al. |
| 2014/0121774 A1 | 5/2014 | Glerum et al. |
| 2014/0148902 A1 | 5/2014 | Dickson et al. |
| 2014/0243982 A1 | 8/2014 | Miller |
| 2014/0277473 A1 | 9/2014 | Perrow |
| 2014/0277509 A1 | 9/2014 | Robinson et al. |

(56)                    References Cited

U.S. PATENT DOCUMENTS

| | | | |
|---|---|---|---|
| 2014/0277510 A1 | 9/2014 | Robinson et al. | |
| 2014/0296984 A1 | 10/2014 | Etminan | |
| 2014/0363610 A1* | 12/2014 | Sameoto | B29C 43/003 |
| | | | 428/92 |
| 2015/0012097 A1 | 1/2015 | Ibarra et al. | |
| 2015/0012098 A1 | 1/2015 | Eastlack et al. | |
| 2015/0012101 A1 | 1/2015 | Glerum et al. | |
| 2015/0073553 A1 | 3/2015 | Barriero et al. | |
| 2015/0112438 A1 | 4/2015 | McLean | |
| 2015/0209042 A1 | 7/2015 | Webster | |
| 2015/0328379 A1 | 11/2015 | Carr et al. | |
| 2015/0335434 A1 | 11/2015 | Patterson et al. | |
| 2016/0022434 A1 | 1/2016 | Robinson | |
| 2016/0067104 A1 | 3/2016 | Sarangapani et al. | |
| 2016/0135960 A1 | 5/2016 | Grotz | |
| 2016/0166396 A1 | 6/2016 | McClintock | |
| 2016/0183990 A1 | 6/2016 | Koizumi et al. | |
| 2016/0324654 A1 | 11/2016 | Loebl et al. | |
| 2017/0042695 A1 | 2/2017 | Foley et al. | |
| 2017/0105844 A1 | 4/2017 | Kuyler et al. | |
| 2017/0319758 A1 | 11/2017 | Eddy et al. | |
| 2018/0256336 A1 | 9/2018 | Mueller et al. | |
| 2018/0296343 A1* | 10/2018 | Wei | B33Y 50/00 |
| 2018/0318101 A1 | 11/2018 | Engstrom | |
| 2018/0338838 A1 | 11/2018 | Cryder et al. | |
| 2019/0076266 A1 | 3/2019 | Trudeau et al. | |
| 2019/0192303 A1 | 6/2019 | Gallagher et al. | |
| 2019/0343650 A1 | 11/2019 | Petersheim et al. | |
| 2020/0113700 A1 | 4/2020 | Ogawa | |
| 2020/0345465 A1 | 11/2020 | Ishiwata | |
| 2021/0022882 A1 | 1/2021 | Dang et al. | |
| 2021/0038403 A1 | 2/2021 | Neary | |
| 2021/0228360 A1 | 7/2021 | Hunt et al. | |
| 2021/0259849 A1 | 8/2021 | Robinson et al. | |
| 2021/0267772 A1 | 9/2021 | Trieu | |
| 2021/0330431 A1 | 10/2021 | Yang et al. | |
| 2022/0133443 A1 | 5/2022 | Lovera Prado | |
| 2022/0409390 A1 | 12/2022 | McLean | |
| 2023/0053789 A1 | 2/2023 | Greenhalgh | |
| 2023/0130542 A1 | 4/2023 | McLean et al. | |
| 2023/0414368 A1 | 12/2023 | Robinson et al. | |
| 2024/0074872 A1 | 3/2024 | Robinson | |
| 2024/0081955 A1 | 3/2024 | Robinson et al. | |
| 2024/0148514 A1 | 5/2024 | Keller et al. | |
| 2024/0423804 A1 | 12/2024 | Robinson | |
| 2024/0423813 A1 | 12/2024 | Robinson | |
| 2025/0120815 A1 | 4/2025 | Robinson | |
| 2025/0121124 A1 | 4/2025 | Robinson | |
| 2025/0302637 A1 | 10/2025 | McLean et al. | |

FOREIGN PATENT DOCUMENTS

| | | | |
|---|---|---|---|
| DE | 102012023042 | B3 | 11/2013 |
| EP | 0674880 | A1 | 10/1995 |
| EP | 1013236 | A1 | 6/2000 |
| EP | 1138268 | A1 | 10/2001 |
| EP | 1169971 | A2 | 1/2002 |
| EP | 1274357 | B1 | 2/2006 |
| EP | 1504735 | B1 | 1/2008 |
| EP | 2275047 | A2 | 1/2011 |
| EP | 2386274 | A1 | 11/2011 |
| FR | 2696091 | A1 | 4/1994 |
| FR | 2762778 | A1 | 11/1998 |
| FR | 2771282 | A1 | 5/1999 |
| JP | 2002523179 | A | 7/2002 |
| JP | 2004525702 | A | 8/2004 |
| JP | 2005007048 | A | 1/2005 |
| JP | 2005040600 | A | 2/2005 |
| KR | 100897928 | B1 | 5/2009 |
| MX | 2009005457 | A | 6/2009 |
| WO | WO00/012033 | A1 | 3/2000 |
| WO | WO00/023013 | A1 | 4/2000 |
| WO | WO00/078238 | A1 | 12/2000 |
| WO | WO2002/076351 | A1 | 10/2002 |
| WO | WO2004/064653 | A1 | 8/2004 |
| WO | WO2009/046517 | A1 | 4/2009 |
| WO | WO2009/151734 | A1 | 12/2009 |
| WO | WO2010/009168 | A1 | 1/2010 |
| WO | WO2010/019783 | A2 | 2/2010 |
| WO | WO2010/078520 | A8 | 7/2010 |
| WO | WO2010/144636 | A1 | 12/2010 |
| WO | WO2011/007240 | A1 | 1/2011 |
| WO | WO2011/094062 | A1 | 8/2011 |
| WO | WO2011/124787 | | 10/2011 |
| WO | WO2012/012771 | A1 | 1/2012 |
| WO | WO2012/078174 | A1 | 6/2012 |
| WO | WO2013/142480 | A1 | 9/2013 |
| WO | WO2013/158294 | A1 | 10/2013 |
| WO | WO2013/159097 | A1 | 10/2013 |
| WO | WO2014/008168 | A2 | 1/2014 |
| WO | WO2014/018325 | A1 | 1/2014 |
| WO | WO2014/025901 | A2 | 2/2014 |
| WO | WO2014/062953 | A1 | 4/2014 |
| WO | WO2014/078008 | A1 | 5/2014 |
| WO | WO2014/145982 | A1 | 9/2014 |
| WO | WO2014/145995 | A2 | 9/2014 |
| WO | WO2014/152337 | A1 | 9/2014 |
| WO | WO2015/030228 | A1 | 3/2015 |
| WO | WO2015/063721 | A1 | 5/2015 |
| WO | WO2016/069796 | A1 | 5/2016 |
| WO | WO2016/130878 | A1 | 8/2016 |
| WO | WO2023/250408 | A1 | 12/2023 |
| WO | WO2023/250449 | A1 | 12/2023 |

OTHER PUBLICATIONS

Dumas et al.; Multiscale grooved titanium processed with femto-second laser influences mesenchymal stem cell morphology, adhesion, and matrix organization; Journal of Biomedical Materials Research Part A; 100(11); pp. 3108-3116; Nov. 2012.

Johnson & Johnson; DePuy Synthes Acquires Interventional Spine Expandable Cage Technology to Accelerate Growth in Spine; Medical technologies; 4 pages; retrieved from the internet (https://www.jnj.com/media-center/press-releases/depuy-synthes-acquires-interventional-spine-expandable-cage-technology-to-accelerate-growth-in-spine); Jan. 3, 2017.

Martinez-Calderon et al.; Surface micro-and nano-texturing of stainless steel by femtosecond laser for the control of cell migration; Scientific reports; 6(1); 3629; pp. 1-10; Nov. 2, 2016.

Opticage; The ultimate choice for interbody fusion; (Company Brochure); Interventional Spine; 2 pages; retrieved from the internet (https://thespinemarketgroup.com/wp-content/uploads/2016/07/Opticage-Two-Pager-5069-Rev.-B-V4.1-1.pdf) on Jan. 5, 2026.

Young; FDA Clears Interventional Spines Opticage Device; Orthapedics This Week; 2 pages; retrieved from the internet (https://ryortho.com/2015/11/fda-clears-interventional-spines-opticage-device/#:~:text=Interventional%20Spine,%20Inc,%20a%20privately,new%20Opticage%20in%20January%202016); Nov. 17, 2015.

Robinson et al.; U.S. Pat. Appl. # U.S. Appl. No. 19/362,332 entitled "Implant with enhanced osteoinductivity," filed Oct. 17, 2025.

* cited by examiner

IMPLANT FUSION DEVICE AND METHOD OF MANUFACTURING

FIELD OF THE INVENTION

The present invention relates to an implant fusion device and a method of manufacturing an implant fusion device. More particularly an orthopedic or spinal implant configured to be implanted between adjacent vertebrae or within a gap in a bone or between bones, the device having a manufactured body structure simulating the physical characteristics of trabecular bone, but with improved osteoinductive features on the exterior surface wherein the device is fabricated using 3D printing. Alternatively, the implant may be made through 3D printing in a manner that results in a relatively or completely solid structure, but with a surface that mimics trabecular bone structure.

BACKGROUND OF THE INVENTION

Surgical implantation of interbody cages is typically used to provide support along the spinal column in cases where a portion of the patient's intervertebral anatomy has become weakened, diseased, or destroyed. Such support systems are also commonly used following a discectomy, where an intervertebral disc is surgically removed.

Most commonly, existing support systems typically operate by inhibiting normal movement between the adjacent vertebrae, thereby stabilizing these vertebrae at fixed positions relative to one another, with the mechanical body of the supporting structure providing the needed support along the patient's spinal column. Such supporting systems are typically made of stainless steel, titanium, titanium alloy, polymer (e.g., an organic polymer thermoplastic such as polyether ether ketone (PEEK)), carbon fiber, or ceramic and they are designed to permanently remain within the patient's body.

It is beneficial, in addition to fixation, to try to stimulate bone growth between the adjacent vertebrae. To do so, spine surgeons often use bone graft material in addition to fixation devices. Bone graft doesn't heal or fuse the spine immediately; instead, bone graft provides a foundation or scaffold for the patient's body to grow new bone. Bone graft can stimulate new bone production. When new bone grows and solidifies, fusion occurs. Although instrumentation (e.g., screws, rods) is often used for initial stabilization (post-operative), it is the healing of bone that welds vertebrae together to create long-term stability. There are two general types of bone grafts: real bone and bone graft substitutes. Real bone can come from the patient (autograft) or from a donor bone (allograft). Also used in these types of surgery are bone substitute, osteoinductive agents, stem cell products, bone morphogenic proteins, and bone cement.

There is a need for improved systems and methods for spinal fusion devices. Ideally, the spinal fusion implant device has features that facilitate new bone growth to achieve fusion of the adjacent vertebrae.

Definitions

As used herein and in the claims:

3D printing, or additive manufacturing, is the construction of a three-dimensional object from a CAD model or a digital 3D model. The term "3D printing" can refer to a variety of processes in which material is deposited, joined or solidified under computer control to create a three-dimensional object, with material being added together, typically layer by layer.

Nanotechnology is the engineering of functional systems at the nanometer scale. This covers both current work and concepts that are more advanced. In its original sense, nanotechnology refers to the projected ability to construct items from the bottom up, using techniques and tools being developed today to make complete, high-performance products. Alternatively, nanostructure may be developed through subtractive processes.

Cortical or compact bone can be distinguished macroscopically from cancellous or trabecular bone. Cortical bone is a dense tissue that contains less than 10% soft tissue. Cancellous or spongy bone is made up of trabeculae, shaped as interconnected plates or rods and arced structures interspersed between voids in the mineral structure that contain blood cells in the marrow space which represents more than 75% of the cancellous bone volume.

Microtechnology/Laser Micro Machining Although similar in concept to traditional machining operations, laser micro machining (laser micromachining) is capable of creating extremely small features—generally under 1 mm, and in some cases only a few microns in size—with a high degree of repeatability and without causing significant structural damage to the surrounding material.

Micron ($\mu m$) Microns, also known as micrometers (represented as $\mu m$) are a length of measurement equal to one millionth of a meter. (1,000 $\mu m$ is equal to 1 mm)

Nanotechnology: One nanometer (nm) is one billionth, or 10-9, of a meter. By comparison, typical carbon-carbon bond lengths, or the spacing between these atoms in a molecule, are in the range 0.12-0.15 nm, and a DNA double-helix has a diameter around 2 nm. On the other hand, the smallest cellular life-forms, the bacteria of the genus *Mycoplasma*, are around 200 nm in length. By convention, nanotechnology is taken as the scale range 1 to 100 nm following the definition used by the National Nanotechnology Initiative in the US. The lower limit is set by the size of atoms (hydrogen has the smallest atoms, which are approximately a quarter of a nm kinetic diameter) since nanotechnology must build its devices from atoms and molecules. The upper limit is more or less arbitrary but is around the size below which the phenomena not observed in larger structures start to become apparent and can be made use of in the nano device. These new phenomena make nanotechnology distinct from devices which are merely miniaturized versions of an equivalent macroscopic device; such devices are on a larger scale and come under the description of microtechnology.

Trabecular bone is a highly porous (typically 75-95%) form of bone tissue that is organized into a network of interconnected rods and plates and arcs called trabeculae which surround pores that are filled with cellular bone marrow.

SUMMARY OF THE INVENTION

The present invention according to a first embodiment is a method of making a spinal implant fusion device having the steps of: fabricating an implant body structure using 3D printing to create the implant body structure; additively building the body structure having a superior load bearing surface and an inferior load bearing surface and a wall structure; and wherein the body structure has at least a portion of the body structure having a plurality of interconnected struts forming porous walls with openings or passages extending inwardly from an exterior surface to a depth of 1.0 mm or greater forming a porous portion with a void volume to solid mass volume mimicking trabecular bone.

Alternatively, the 3D printed structure may be completely or substantially solid with a surface structure comprised of the interconnected arcs that are raised, or created like troughs that appear to be cut into the surface but were created through 3D printing.

The average or nominal ratio of void volume to mass volume in the porous portion is in the range of 65 percent or more, preferably 75 percent replicating that of trabecular bone in an adult male. The struts of the porous walls are curved or arch shaped with openings communicating with adjacent walls. The porous portion of the implant body structure extends at least partially across the implant body structure exterior surfaces forming conduits for fluid passage throughout the device. The curved or arch shaped struts of the walls create a load bearing capacity to withstand vertical loads without collapsing. The implant fusion device has the superior load bearing surface and the inferior load bearing surface having nano channels etched on exposed surfaces. The etching created through a subtractive laser process. Alternatively, the 3D printed structure may be solid or relatively solid with a 3D printed surface structure that mimics trabecular bone structure as described above, with a laser etched subtractive process then applied that results in a nanotechnology level of surface which is biologically active for the induction of bone formation and growth.

In a second embodiment, a method of making a spinal implant fusion device has the steps of: providing a 3D printed implant body structure; and subsequent subtractive laser etching which results in nanometer-level structure on at least a portion of a surface or surfaces of the implant body structure, the nanometer structure creating new bone growth attachment features to enhance osteoinductivity of the spinal implant or orthopedic fusion device.

The laser etched nanometer structural features are made into a network of features in either a random pattern or an organized pattern. The laser etching is formed by emitting laser beams unobstructed to the surfaces of the implant. The method of making a spinal implant fusion device or other orthopedic or bone implant further has the step of moving a laser about the implant body structure to create the network of features or the method has the step of moving the implant body structure about a laser to create the network of features.

The present invention also has the combination of 3D printing and laser etching in a method of making a spinal implant fusion device or orthopedic or bone device having the steps of: fabricating an implant body structure using 3D printing to create the implant body structure; additively building the body structure having a superior load bearing surface and an inferior load bearing surface and a wall structure; wherein the body structure has at least a portion of the body structure having a plurality of interconnected struts forming porous walls with openings extending inwardly from an exterior surface to a depth of 1.0 mm or greater forming a porous portion with a void volume to solid mass volume mimicking trabecular bone; and laser etching nano channels on at least a portion of the exterior surface or surfaces of the implant body structure, the nano channels creating new bone growth attachment features to enhance osteoinductivity of the spinal implant fusion device.

The method of making a spinal implant device or orthopedic device or bone implant device wherein the structure is produced through a 3D printing additive process, which is then further processed with a laser etching technology that results in a nanotechnology structure at the surface that facilitates bone attachment and growth. The 3D printing additive process creates a structure at the implant surface that mimics trabecular bone structure.

The spinal implant device or orthopedic device or bone implant device can be produced through a 3D printing additive process in a biocompatible material or materials that is further processed through a subtractive laser etching process that results in a surface or surfaces with nanometer-level structural elements. The 3D printing additive process results in surface features that mimic trabecular bone structure.

BRIEF DESCRIPTION OF THE DRAWINGS

The invention will be described by way of example and with reference to the accompanying drawings in which.

DETAILED DESCRIPTION OF THE INVENTION

With reference to FIGS. 1-4 and 7, various views of the implant fusion device of the present invention are shown.

Figure 1:
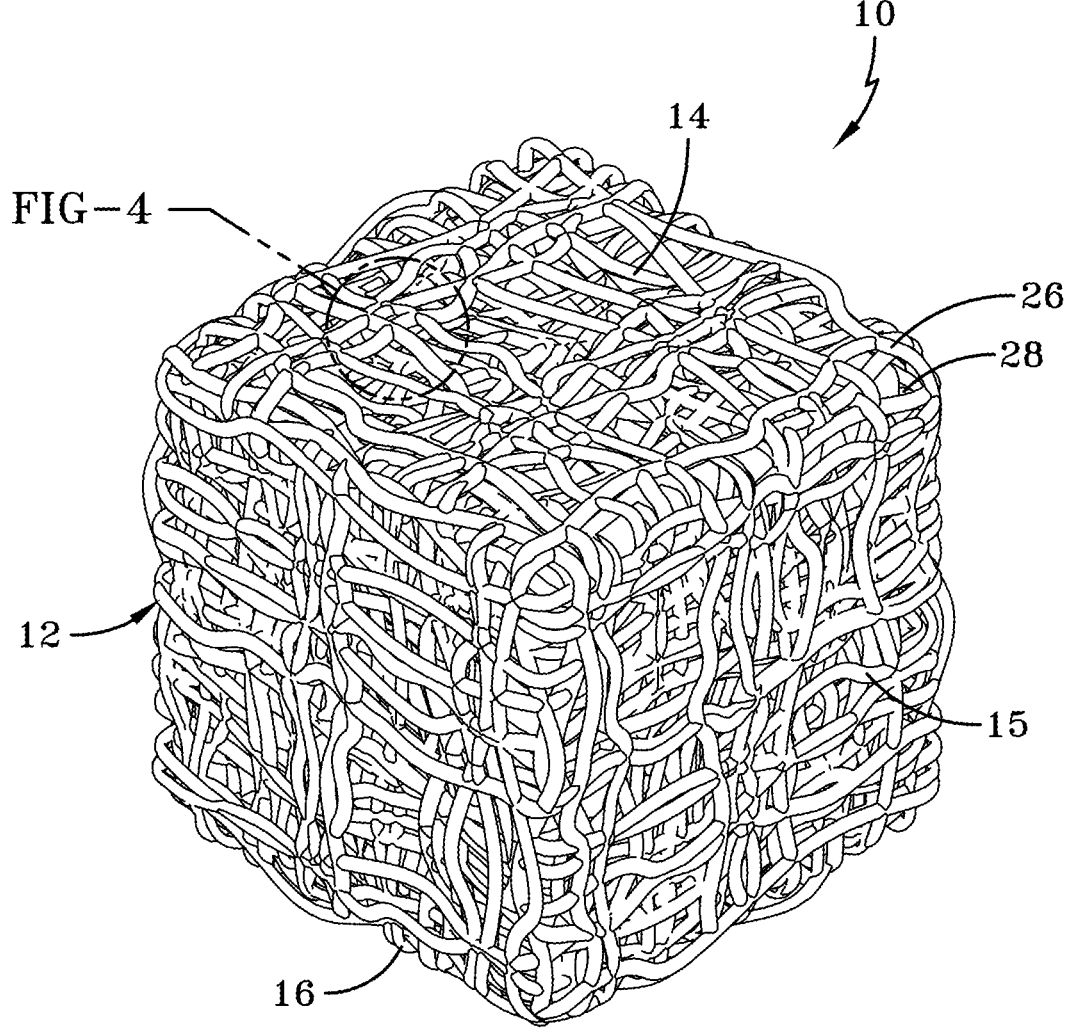
FIG. 1 is an exemplary embodiment of the spinal implant fusion device of the present invention.

As shown in FIG. 1, the exemplary embodiment is shown as a cube having six sides. The configuration of the implant device 10 as illustrated has a first or superior surface 14, a second or inferior surface 16 and side surfaces 15 that surround and form the exterior surfaces of the implant body structure 12. The first surface 14 and second surface 16 provide the implant fusion device 10 with surfaces that upon implantation between two adjacent vertebral bodies will support the bone structure of the adjacent vertebral bodies. These first and second surfaces 12, 16 are in direct contact with the bone structure of the adjacent vertebral bodies of the patient upon implantation of the device 10 for a procedure where an implant fusion device is being implanted to correct a degenerative condition or other condition in a patient.

As shown, the exemplary embodiment is merely example of configurations that can be employed to make the present invention. Any number of shapes can be used in this configuration and can be any number of polygonal shapes of various shapes and sizes as long as they are sufficient to support the load between the adjacent vertebral bodies to make a proper implant fusion device.

For example, the cube shape in FIG. 1 could also be rectangular, oblong or elongated. A cylindrical device with a circular side can be used. Similarly, the device can have a pentagonal or hexagonal shape where the sides are not circular. Any number of these alternative configurations can be employed using the implant device of the present invention as will be discussed later.

Figure 2:
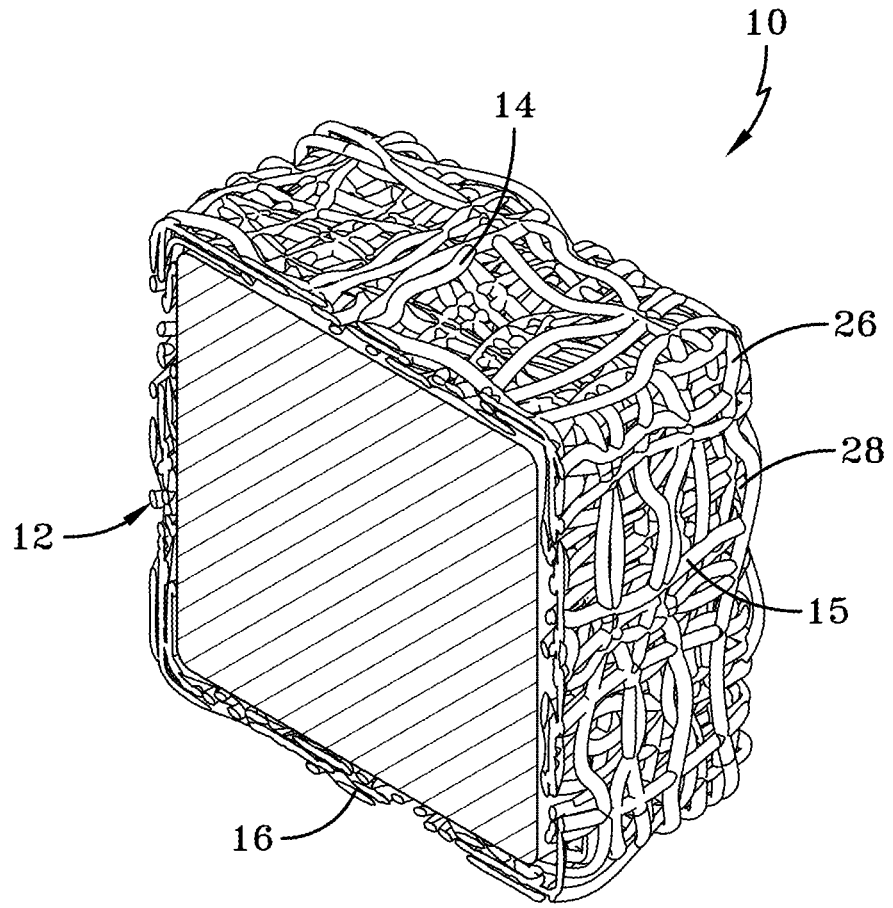
FIG. 2 is a cross-sectional view of the implant device taken along lines 2-2 of FIG. 1.
Figure 5:
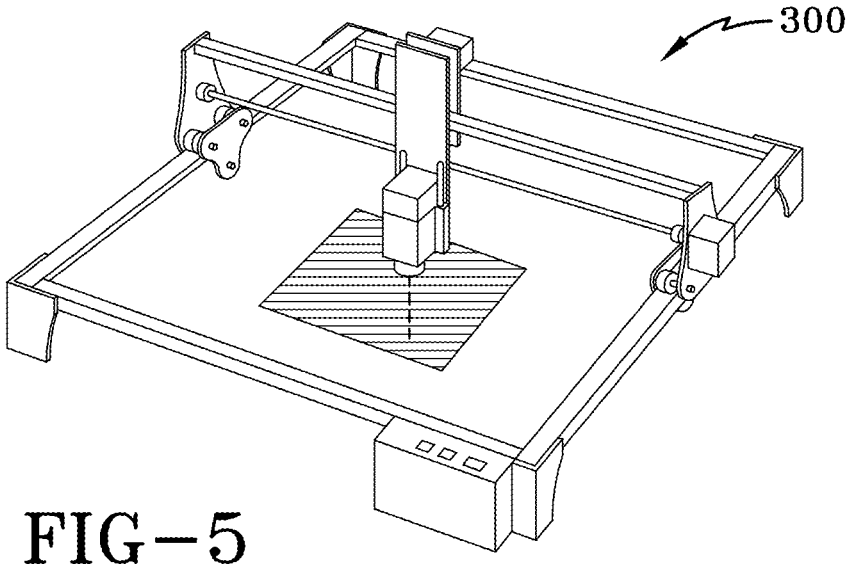
FIG. 5 is an exemplary 3D printer.

With reference to FIG. 2, a cross-sectional view is taken from FIG. 1. The cross-sectional view shows the interior structure of the implant device 10 of the present invention. As shown, the body structure 12 of the implant device 10 of the present invention has a solid central area or region and an external region with ratio of void volume to mass volume that is relatively high and replicates trabecular bone, more particularly cancellous trabecular bone wherein the high porosity creates open pathways for fluid to move in and out similar to what happens in natural bone. The body structure 12 of the implant device 10 is formed by 3D or additive printing forming exterior portions made with a plurality of interconnected struts 26, the struts 26 being curved or arched and spaced between connections with openings 28 forming a porous wall having a porosity that replicates that of an adult male or female depending on the implant being produced. An exemplary 3D printer 300 is shown in FIG. 5. It is important to note that this high ratio of porosity is extended towards a central region of the device 10. As the device extends from the perimeter to the exterior surfaces 14, 15, 16 of the implant device 10 this ratio of void volume to mass volume can be reduced dramatically, this occurs as the 3D building of the device is being performed. As such, the exterior surfaces 14, 15, 16 can have the porous walls extend approximately 1 mm or greater into the interior from the exterior surface with a center portion of the body structure having a much reduced ratio of void volume to mass volume. This reduced ratio is more tightly compacted creating a core inside the implant device with a porous structure around the entire implant device 10. This enhances the structural strength of the device 10 and provides a superior bone generating exterior surface or surfaces of the more open porosity with the interior core of the body structure 12 providing high strength.

Optionally, this porous structure of interconnected struts 26 can be made to extend throughout the implant body structure if so desired. In practice, it has been found that the depth of the surfaces mimicking the trabecular bone of at least 1 mm in depth is ideal for new bone formation and therefore the 3D manufacturing of the implant can be made simpler and less expensively by limiting the depth to 1 mm or greater. Additionally, the superior 14 and inferior 16 surface should have the porous trabecular features, but the side walls could be solid as an optional way to manufacture the implant.

Figure 3:
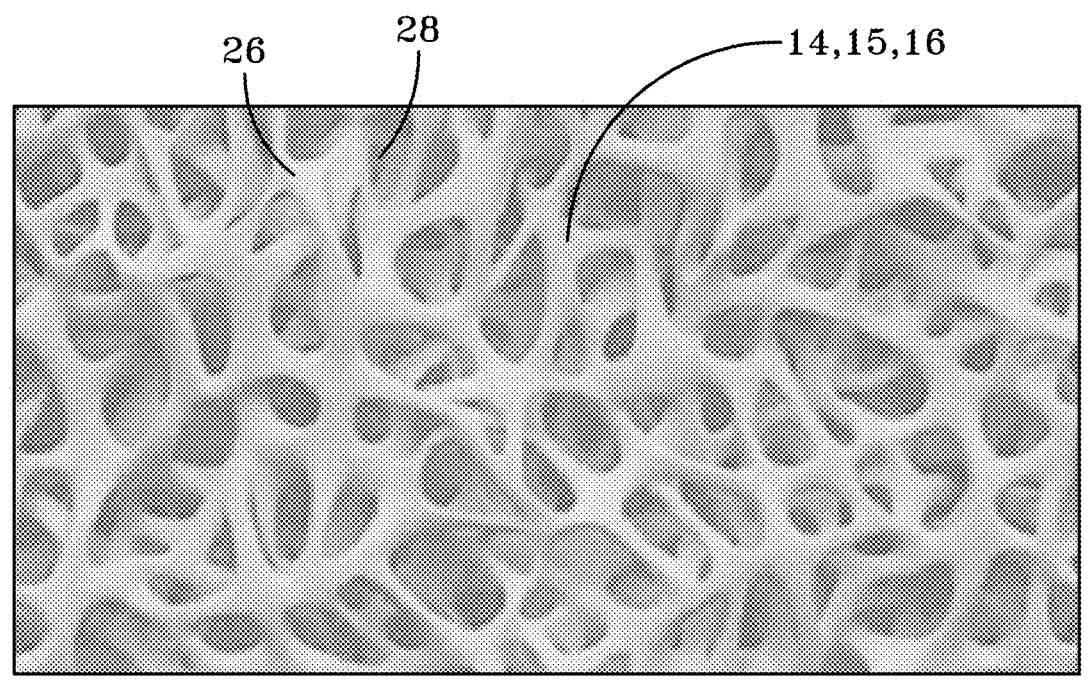
FIG. 3 is an enlarged view of a portion of an exterior surface of the present invention depicting the surface, the surface being undulating with protruding and depressed features at the surface mimicking trabecular bone.
Figure 4:
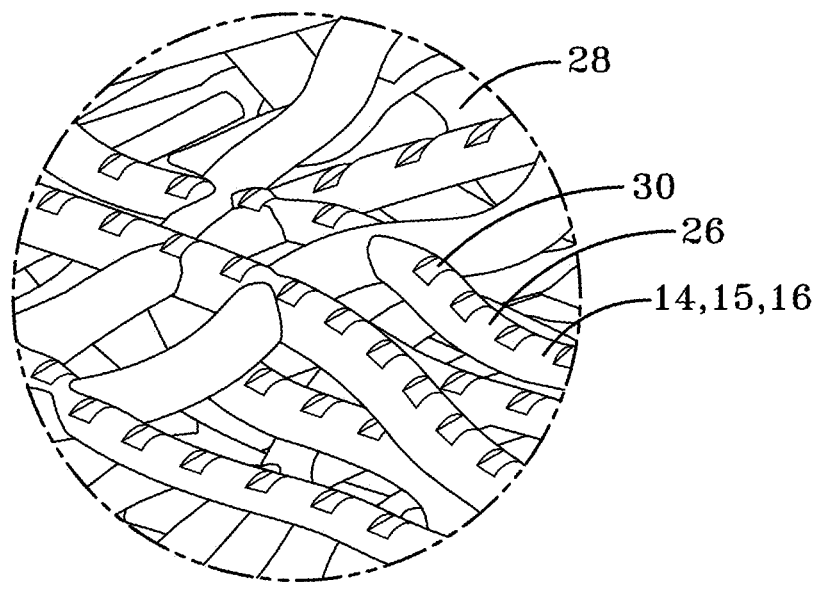
FIG. 4 is an enlarged view of the surface showing laser etched nano channels.

With reference to FIGS. 3 and 4, a portion of the exterior surface 14, 15, 16 is shown. This porous exterior surface can be along the surface of the first surface 14, second surface 16 or side surface 15 or all of these surfaces.

Figure 7:
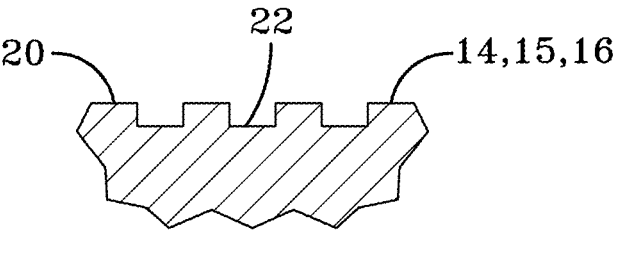
FIG. 7 is a simplified schematic outline of a portion of an exterior surface showing projections and channels or troughs of an alternative embodiment.

FIG. 7 is a simplified schematic outline of a portion of an exterior surface of an alternative embodiment, this exterior surface 14, 15, 16 has an undulating feature such that the exterior surface has protrusions 20 projecting outwardly slightly and channels or troughs 22 that are recessed slightly. These features create an undulating surface that enhances the ability of the device 10 to create space between the adjacent vertebrae when the device 10 is implanted. Additionally, this entire surface is then treated using laser etching to create nano channels 30 best shown in FIG. 4.

Figure 6:
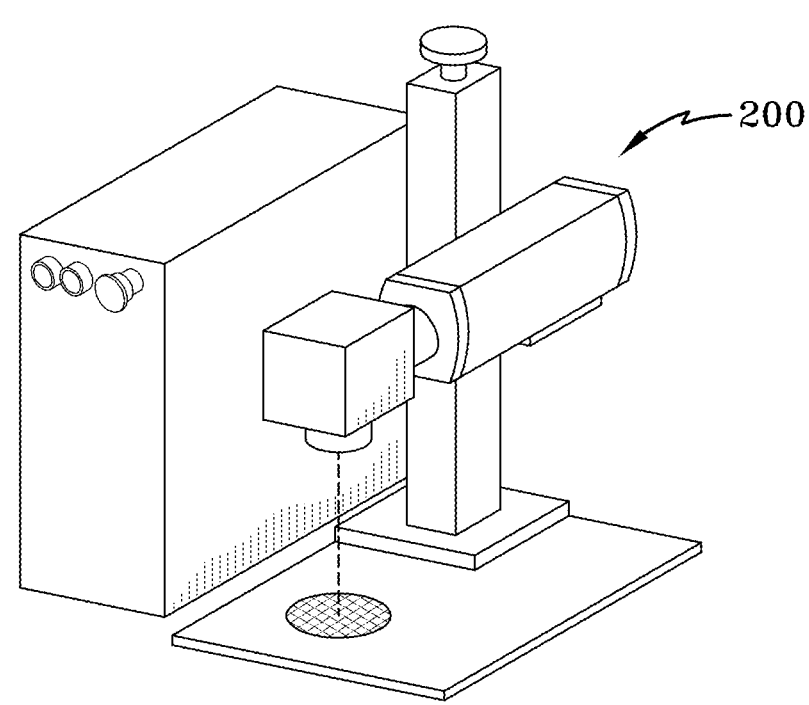
FIG. 6 is an exemplary laser etching machine.
Figure 8A:
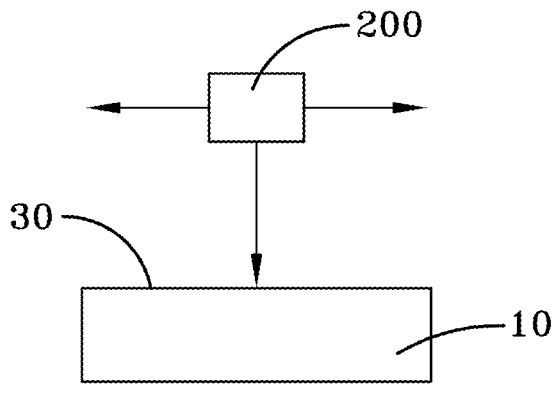
FIG. 8A is a simplified schematic drawing showing the making of laser etched channels using a moving laser machine.
Figure 8B:
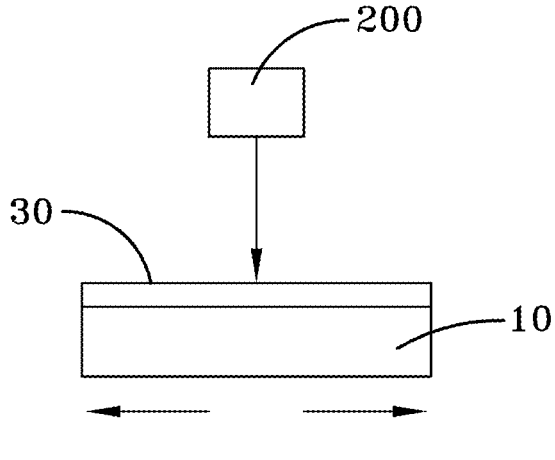
FIG. 8B is a simplified schematic drawing showing the making of laser etched channels using a fixed laser machine with the implant being moved.

In FIG. 6, an exemplary laser etching machine 200 is illustrated that can be used to form nano channels. These nano channels 30 can be laid in a network 18 either in an organized uniform pattern or a random non-uniform pattern throughout the exterior surfaces 14, 15, 16. Ideally, these nano channels 30 are created at least along the first and second surfaces 14, 16 of the implant device 10. The nano channels 30 are small laser etched cuts that can be laid out along the entire exterior surfaces in a subtractive laser etching process. These nano channels 30 created by laser etching can be made either by moving the laser 200 about the exterior surface 14, 15, 16 of the implant device to form the nano channels 30 as shown in FIG. 8A; or the implant device 10 can be moved relative to the laser such that the nano channels 30 are laid onto the exterior surfaces 14, 15, 16 as shown in FIG. 8B. The nano channel features individually create an improved osteoinductive effect at the surface of the implant device 10. This means that the formation of new bone once implanted into the patient can be accelerated and the network 18 of nano channels 30 provide features that help assist in providing attachment locations for the new bone formation. This is an important feature that is provided in the current invention and is ideal in that it does not require smooth or flat exterior surfaces to form the channels which are effectively etched or burned into the exterior surface. The channels can be created as long as the path of the laser beam is unobstructed. As a result, even though the porous walls of exterior surfaces have slight undulations 20, 22 and openings, the network 18 of nano-channels 30 can be formed regardless of this and not limited to the topography of exterior surfaces commonly found in implant devices that are molded or otherwise have smooth exterior surfaces. In fact, the nano channels 30 can be found formed at varying depths where the openings allow the laser beam to pass. The nano channels preferably have a width and a depth of 10 nano meters or greater up to 1000 nano meters. These features are very small and unlike micro channel laser etching, the nano channels can be etched extremely quickly due to their small size.

Figure 9:
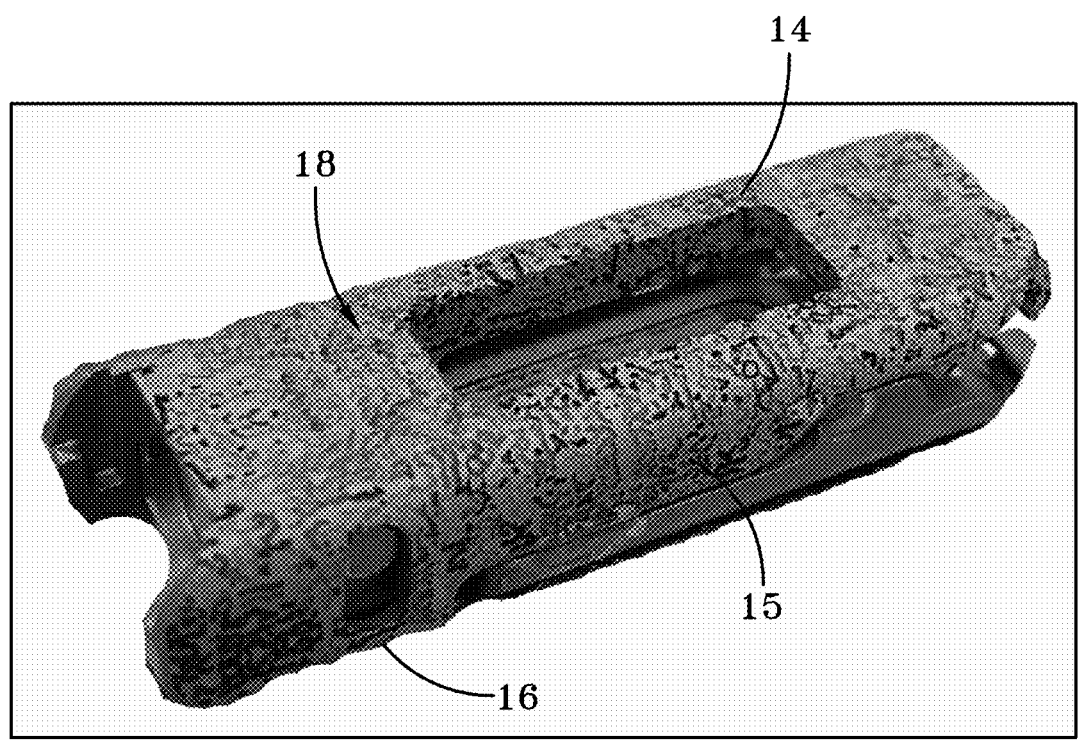
FIG. 9 is a perspective view of an expandable spinal implant device made according to the present invention.
Figure 10:
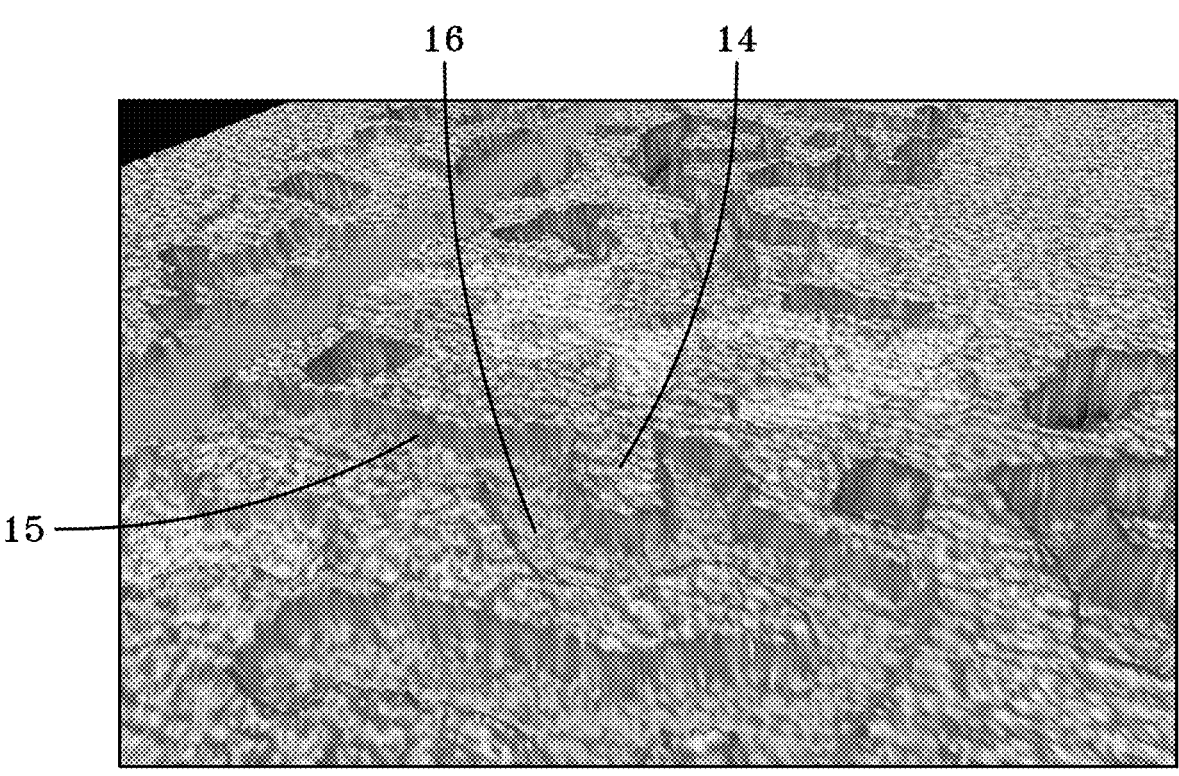
FIG. 10 is an enlarged view of a surface made using the process of the present invention.
Figure 11:
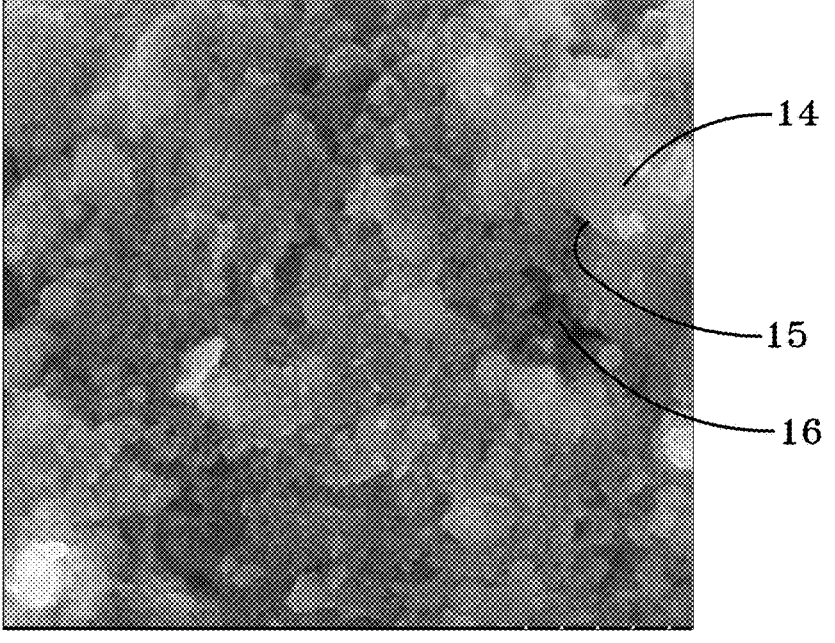
FIG. 11 is a magnification of the surface made using the process of the present invention.

With reference to FIG. 9, a perspective view of an expandable spinal implant device 10 is shown having been made according to the methods described above. As shown, surfaces 14, 15, 16 have the porous feature for enhanced osteoinductivity for encouraging new bone to fuse to the device 10 after being installed in the disc space. The device 10, as shown, is in a partially expanded condition. The level of expansion can be raised to a higher amount or lowered to a closed position for insertion. The treated surfaces 14, 15, 16 are more refined than those shown in FIG. 1 and as can be seen in the enlarged view of FIG. 10 which illustrates the appearance of the trabecular bone mimicking surface. FIG. 11 is a highly magnified image that shows the nano features of the surface in which the entire width of the image shown is only about 2 microns. The scale can be appreciated in the image shown in FIG. 9 of the textured cage itself which is 35 mm in length and the grooves can be easily seen by eye without magnification. It is noted any implant device can be treated post manufacturing to create these surfaces on an existing implant device. Furthermore, the process can be used to form the surfaces on any number of implants where osteoinductive bone grown enhancement is desired. These can be bone fasteners, pedicle screws, cervical plates, spinal fusion cages and any bone contacting implant device that benefits from bone growth around the surface of the implant. The materials the implant device is made of can be any suitable implant material of metal, plastic or bone and the benefits of enhanced osteoinductivity can be achieved.

The method of making a spinal implant device or orthopedic device or bone implant device according to the present invention made by 3D printing and a post process with a laser etching process resulting in nanometer scale of surface structure that is biologically active in inducing bone growth. In addition, a 3D printing orthopedic or spinal device in which a surface pattern mimicking trabecular bone with arching structure mimicking trabecular bone formation that is created through the 3D printing process that either appears raised from the surface or recessed into the surface, either way it is made through the additive manufacturing process. Further, laser etched surface results in a nanometer scale structure that is active in bone growth formation. The laser etching results in a nanometer scale surface structure because the heat of the laser does not cause a significant melt at the surface that would remove material from the ablation from the nanometer scale of the structure rather than the laser heating it up so that it sears the surface through melting.

These and other aspects of the present invention are believed to greatly enhance the ability of the present device made by 3D printing and laser etching to provide an improved implant fusion device.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of making a spinal implant device or orthopedic device or bone implant device, the method comprising: producing a structure through a three-dimensional (3D) printing additive process so that at an exterior portion of the structure comprises a plurality of interconnected struts that are curved or arched and spaced between open connections forming a porous wall having a porosity of between 75%-95%, wherein the structure is then further processed, after the 3D printing additive process is complete, with a laser etching technology that results in a nanotechnology structure comprising a plurality of nano channels arranged in a network on at least a first and second exterior surface of the interconnected struts that facilitates bone attachment and growth, wherein the laser etching is independent of topography of the exterior surface and wherein the plurality of nano channels have variable depth.

2. The method of making a spinal implant device or orthopedic device or bone implant device of claim 1, wherein the 3D printing additive process creates a structure at the exterior surface that mimics trabecular bone structure.

3. A method of making a spinal implant device or orthopedic device or bone implant device comprises the steps of:

fabricating an implant body structure using three-dimensional (3D) printing to create the implant body structure;

additively building the body structure having a superior load bearing surface and an inferior load bearing surface and a wall structure, wherein an outer surface or surfaces of the body structure comprises a plurality of interconnected struts that are curved or arched and spaced between open connections forming a porous portion having a porosity of between 75%-95%; and laser etching nano channels on at least a portion of interconnected struts of at least a first and second outer surface of the implant body structure after the 3D printing is completed, wherein the laser etching is independent of topography of the first and second outer surface and wherein the nano channels have variable depth;

wherein the body structure has at least a portion having the plurality of interconnected struts forming porous walls with openings extending inwardly from an exterior surface to a depth of 1.0 mm or greater forming the porous portion with a void volume to solid mass volume mimicking trabecular bone.

4. The method of making a spinal implant device or orthopedic device or bone implant device of claim 3, wherein the average or nominal ratio of void volume to mass volume in the porous portion is in a range of 65 percent or more, replicating that of trabecular bone in an adult male.

5. The method of making a spinal implant device or orthopedic device or bone implant device of claim 4, wherein the struts of the porous walls are curved or arch shaped with openings communicating with adjacent walls.

6. The method of making a spinal implant device or orthopedic device or bone implant device of claim 5, wherein the porous portion of the implant body structure extends at least partially across the implant body structure to the exterior surfaces forming conduits for fluid passage throughout the device.

7. The method of making a spinal implant device or orthopedic device or bone implant device of claim 6, wherein the curved or arch shaped struts of the porous walls create a load bearing capacity to withstand vertical loads without collapsing.

8. The method of making a spinal implant device or orthopedic device or bone implant device of claim 3, wherein the implant device has the superior load bearing surface and the inferior load bearing surface, each load bearing surface having nano channels etched on exposed surfaces.

9. The method of making a spinal implant device or orthopedic device or bone implant device of claim 4, wherein the nano channels are made into a network of features in either a random pattern or an organized pattern.

10. The method of making a spinal implant device or orthopedic device or bone implant device of claim 9, wherein the nano channels are formed by emitting laser beams unobstructed to surfaces within a path of the laser beams.

11. The method of making a spinal implant fusion device of claim 9, wherein the implant body structure is stationary and a laser moves about the implant body structure to create the network of features or wherein a laser is stationary and the implant body structure moves relative to the laser to create the network of features.

12. The method of making a spinal implant device or orthopedic device or bone implant device of claim 3, further comprises the steps of:

wherein the step of fabricating includes providing the implant body structure; and the nano channels creating new bone growth attachment features to enhance osteoinductivity of the device.

13. The method of making a spinal implant device or orthopedic device or bone implant device of claim 12, wherein the laser etched nano channels are made into a network of features in either a random pattern or an organized pattern.

14. The method of making a spinal implant device or orthopedic device or bone implant device of claim 13, wherein the laser etching is formed by emitting laser beams unobstructed to the exterior surfaces.

15. The method of making a spinal implant device or orthopedic device or bone implant device of claim 14, further comprises the step of moving a laser about the implant body structure to create the network of features.

16. The method of making a spinal implant device or orthopedic device or bone implant device of claim 14, further comprises the step of moving the implant body structure about a laser to create the network of features.

17. A method of making a spinal implant device or orthopedic device or bone implant device comprises the steps of:

fabricating an implant body structure using three-dimensional (3D) printing to create the implant body structure;

additively building the body structure having a superior load bearing surface and an inferior load bearing surface and a wall structure;

wherein the body structure has at least a portion having a plurality of walls with openings extending inwardly from an exterior surface to a depth of 1.0 mm or greater forming a porous portion with a void volume to solid mass volume mimicking trabecular bone so that the exterior surface comprises a plurality of interconnected struts that are curved or arched and spaced between open connections forming the porous portion and having a porosity of between 75%-95%; and after the 3D printing, laser etching nano channels on at least a first and second exterior surface of the interconnected struts on at least a portion of the exterior surface or surfaces of the implant body structure, the nano channels creating new bone growth attachment features to enhance osteoinductivity of the device, wherein the laser etching is independent of topography of the exterior surface and wherein the nano channels have variable depth.

18. The method of making a spinal implant device or orthopedic device or bone implant device of claim 17, wherein the average or nominal ratio of void volume to mass volume of the porous portion is in a range of 65 percent or more, replicating that of trabecular bone in an adult male.

19. The method of making a spinal implant device or orthopedic device or bone implant device of claim 17, wherein one or more of the plurality of walls is curved or arch shaped with openings communicating with adjacent walls.

20. The method of making a spinal implant device or orthopedic device or bone implant device of claim 17, wherein the porous portion of the implant body structure extends across the implant body structure from the exterior surfaces inwardly forming conduits for fluid passage throughout the porous portion of the implant body structure.

21. The method of making a spinal implant device or orthopedic device or bone implant device of claim 20, wherein the curved or arch shaped walls create a load bearing capacity to withstand vertical loads without collapsing.

22. The method of making a spinal implant device or orthopedic device or bone implant device of claim 17, wherein the implant device has the superior load bearing surface and the inferior load bearing surface having nano channels etched on exposed surfaces.

23. The method of making a spinal implant device or orthopedic device or bone implant device of claim 22, wherein the nano channels are made into a network of features in either a random pattern or an organized pattern.

24. The method of making a spinal implant device or orthopedic device or bone implant device of claim 17, wherein the nano channels are formed by emitting laser beams unobstructed to surfaces within a path of the laser beams.

25. The method of making a spinal implant device or orthopedic device or bone implant device of claim 23, wherein the implant body structure is stationary and a laser moves about the implant body structure to create the network of features.

26. The method of making a spinal implant device or orthopedic device or bone implant device of claim 23, wherein a laser is stationary and the implant body structure moves relative to the laser to create the network of features.

* * * * *